US007284956B2

(12) United States Patent
Nose et al.

(10) Patent No.: US 7,284,956 B2
(45) Date of Patent: *Oct. 23, 2007

(54) METHODS AND APPARATUS FOR CONTROLLING A CONTINUOUS FLOW ROTARY BLOOD PUMP

(75) Inventors: Yukihiko Nose, Houston, TX (US); Toshiyuki Shinohara, Houston, TX (US); Ryo Kosaka, Ibaraki (JP); Hirohito Sumikura, Kawagoe (JP)

(73) Assignees: Miwatec Co., Ltd., Kanagawa-Ken (JP); Baylor College of Medicine, Houston, TX (US)

( * ) Notice: Subject to any disclaimer, the term of this patent is extended or adjusted under 35 U.S.C. 154(b) by 736 days.

This patent is subject to a terminal disclaimer.

(21) Appl. No.: 10/291,191

(22) Filed: Nov. 8, 2002

(65) Prior Publication Data

US 2004/0047737 A1 Mar. 11, 2004

Related U.S. Application Data

(63) Continuation-in-part of application No. 10/241,825, filed on Sep. 10, 2002, now Pat. No. 6,817,836.

(51) Int. Cl.
*A61M 1/12* (2006.01)
(52) U.S. Cl. ............... 415/900; 623/3.14; 417/53; 604/151; 128/898
(58) Field of Classification Search ........... 600/160, 600/17, 16; 604/151; 128/898; 415/900; 417/53; 623/3.1, 3.13, 3.14
See application file for complete search history.

(56) References Cited

U.S. PATENT DOCUMENTS

| | | | |
|---|---|---|---|
| 5,399,074 A | 3/1995 | Nose et al. | |
| 5,399,145 A | 3/1995 | Ito et al. | |
| 5,575,630 A | 11/1996 | Nakazawa et al. | |
| 5,601,418 A | 2/1997 | Ohara et al. | |
| 5,683,231 A | 11/1997 | Nakazawa et al. | |
| 5,692,882 A * | 12/1997 | Bozeman et al. | 417/45 |
| 5,713,730 A | 2/1998 | Nose et al. | |
| 5,803,720 A | 9/1998 | Ohara et al. | |
| 5,830,370 A * | 11/1998 | Maloney et al. | 210/780 |
| 5,900,142 A * | 5/1999 | Maloney et al. | 210/179 |
| 5,957,672 A * | 9/1999 | Aber | 417/423.12 |
| 6,129,660 A * | 10/2000 | Nakazeki et al. | 600/17 |
| 6,183,220 B1 | 2/2001 | Ohara et al. | |
| 6,264,635 B1 * | 7/2001 | Wampler et al. | 604/151 |
| 6,605,032 B2 * | 8/2003 | Benkowski et al. | 600/16 |
| 6,623,420 B2 * | 9/2003 | Reich et al. | 600/17 |
| 6,866,625 B1 * | 3/2005 | Ayre et al. | 600/16 |
| 2002/0057989 A1 * | 5/2002 | Afzal et al. | 422/45 |
| 2004/0011740 A1 * | 1/2004 | Bernard et al. | 210/646 |

\* cited by examiner

OTHER PUBLICATIONS

Maslen, Eric H., et al., "Feeback Control Applications in Artificial Hearts," *IEEE Control Systems Magazine*, vol. 18, No. 6, Dec. 1998, pp. 26-34.

*Primary Examiner*—George Manuel
*Assistant Examiner*—Christopher A. Flory
(74) *Attorney, Agent, or Firm*—Lipsitz & McAllister LLC

(57) ABSTRACT

A control system for a continuous flow rotary blood pump is provided. A normal operating range of the blood pump is established. The normal operating range may comprise a normal pump flow range and a normal pressure head range. A target rotational speed of the pump is set in accordance with the normal operating range. A current operating condition of the blood pump is determined. The current operating condition may comprise a current pump flow, a current pressure head, and a current rotational speed of the pump. The current operating condition is compared with the normal operating range. An appropriate control algorithm is selected from a plurality of available control algorithms based on the comparison. The target rotational speed of the pump is adjusted using the selected control algorithm to maintain or recover the normal operating range.

48 Claims, 11 Drawing Sheets

METHODS AND APPARATUS FOR CONTROLLING A CONTINUOUS FLOW ROTARY BLOOD PUMP

The present application is a continuation-in-part of U.S. patent application Ser. No. 10/241,825 filed on Sep. 10, 2002 now U.S. Pat. No. 6,817,836.

BACKGROUND OF THE INVENTION

The present invention relates to the field of rotary blood pumps for assisting a failing human heart. More specifically, the present invention relates to the control of continuous flow rotary blood pump which does not compete with the bodies autonomic system unless the pump flow is detected to be outside of a predetermined range.

Various types of rotary blood pumps have been developed and are currently under development for use as heart assist devices. Compared to pulsatile pumps, rotary blood pumps have several advantages, including smaller size, higher efficiency, and a simpler design.

However, a servo control system for such rotary blood pumps has yet to be developed. Typically, operators have had to monitor patients in the intensive care unit in order to observe the condition of the pump and the patient, as manual intervention is currently required for controlling the rotational speed of the pump.

If such a rotary blood pump is to be used as a left ventricular assist device (LVAS), the pump flow should be increased when the pressurehead is decreased with the fixed rotational speed of the pump, because these parameters automatically adjust to the patient's physiological condition, regardless of the fixed rotational speed of the pump impeller. However, when the venous return suddenly becomes too low because of physiological changes or overpumping, a high negative pressure may result at the inlet port of the pump, which may lead to a suction condition within the atrium and veins, which condition may result in serious injury or even death to the patient.

As rotary blood pumps may be used outside of a hospital environment, for example in nursing homes and home health care environments, it would be advantageous to provide an automated control system for controlling the rotary blood pump, without the need for human supervision and intervention. It would be advantageous for such a control system to operate the rotary blood pump automatically and effectively in response to any sudden changes in the operating conditions of the pump which deviate from a normal operating range.

The methods and apparatus of the present invention provide the foregoing and other advantages.

SUMMARY OF THE INVENTION

The present invention relates to a control system for a continuous flow rotary blood pump, such as a centrifugal pump or an axial flow pump.

In an example embodiment, a normal operating range of the blood pump is established. The normal operating range may comprise a normal pump flow range and a normal pressure head range. A target rotational speed of the pump can then be set in accordance with the normal operating range. A current operating condition of the blood pump is determined. The current operating condition may comprise a current pump flow, a current pressure head, and a current rotational speed of the pump. The current operating condition can then be compared with the normal operating range. An appropriate control algorithm is then selected from a plurality of available control algorithms based on the comparison. The target rotational speed of the pump can then be adjusted using the selected control algorithm to maintain or recover the normal operating range.

The rotary blood pump may be used as a left ventricular assist device or a right ventricular assist device. The blood pump may be an implantable device or an external device.

Measurements of the current pump flow, the current pressure head, and the current rotational speed may be used to determine the current operating condition. The current pump flow, the current pressure head, and the current rotational speed may be measured by one or more sensors. Such sensors may be implantable sensors. Alternatively, such sensors may be external sensors.

The normal operating range may be established by determining a target operating point for the target rotational speed of the pump, which provides a target pump flow and a target pressure head. The normal pump flow range may be within a 20% deviation from the target pump flow. The normal pressure head range may be within a 25% deviation from the target pressure head.

During the normal operating range a normal operating condition control algorithm is selected. In such a case, the target rotational speed of the pump is maintained by applying proportional and derivative gain control to the pump. The proportional and derivative gain control may be applied in accordance with the formula:

$$u = K_p(Y_{target} - Y) + K_d((d/dt)Y_{target} - (d/dt)Y)$$

where u is a driving signal of the pump; Y is the rotational speed of the pump; $Y_{target}$ is the target rotational speed of the pump; $K_p$ is the proportional gain; and $K_d$ is the derivative gain. As an example, $K_p$ may be set to approximately 0.02 and $K_d$ may be set to approximately 0.05.

In the event that the current operating condition is above the normal operating range, a first abnormal operating condition control algorithm is selected. This algorithm decreases the target rotational speed until the normal operating range is recovered. For example, the target rotational speed may be decremented by x rpm every t seconds until the normal operating range is recovered. For a centrifugal pump, research has shown that the normal operating range may be recovered by, for example, decrementing the rotational speed by approximately 150 rpm every 5 seconds. For an axial flow pump, research has shown that the normal operating range may be recovered by, for example, decrementing the rotational speed by approximately 600 rpm every 5 seconds.

In the event that the current operating condition is below the normal operating range, a second abnormal operating condition control algorithm is selected. This algorithm increases the target rotational speed until the normal operating range is recovered. For example, the target rotational speed may be incremented by x rpm every t seconds until the normal operating range is recovered. For a centrifugal pump, research has shown that the normal operating range may be recovered by, for example, incrementing the rotational speed by approximately 150 rpm every 5 seconds. For an axial flow pump, research has shown that the normal operating range may be recovered by, for example, incrementing the rotational speed by approximately 600 rpm every 5 seconds.

However, when the normal operating range cannot be recovered by incrementing the rotational speed of the pump, is determined that a suction condition exists (e.g., due to overpumping). In the event of such a suction condition, a suction condition control algorithm is selected. This algorithm causes the suction condition to be released by continuously decreasing the target rotational speed of the pump to obtain a pump flow free from suction and free from overpumping. Once the suction condition is released, the target rotational speed of the pump is gradually increased to recover the normal operating range.

When releasing the suction condition, the target rotational speed may be continuously decremented by $x_1$ rpm every t seconds. Once the suction condition is released, the target rotational speed may be continuously incremented by $x_2$ rpm every t seconds to recover the normal operating condition.

For a centrifugal pump, research has shown that the suction condition may be released when the rotational speed of the pump is decremented by approximately 150 rpm every 5 seconds (e.g., $x_1$ is approximately 150 rpm and t is approximately 5). The normal operating range can then be recovered by incrementing the rotational speed of the pump by approximately 50 rpm every 5 seconds (e.g., $x_2$ is approximately 50 rpm and t is approximately 5 seconds).

For an axial flow pump, research has shown that the suction condition may be released when the rotational speed of the pump is decremented by approximately 600 rpm every 5 seconds (e.g., $x_1$ is approximately 600 rpm and t is approximately 5). The normal operating range can then be recovered by incrementing the rotational speed of the pump by approximately 200 rpm every 5 seconds (e.g., $x_2$ is approximately 200 rpm and t is approximately 5 seconds).

In an example embodiment of the invention, the pump may comprise a centrifugal pump having magnets implanted in the pump impeller. One or more Hall sensors may be used to detect the position of the pump impeller using the well-known Hall effect. The Hall sensors may be used to detect vertical and/or horizontal movement of the pump impeller. The rpm of the impeller may be adjusted based on the position as detected by the Hall sensors in order to maintain the impeller position in one of a top contact position or a dynamic suspension position. For example, where the Hall sensors detect the impeller position is at or near a bottom contact position, it is desirable to increase the impeller rpm so that the impeller position is moved towards a dynamic suspension position or a top contact position, as blood clots may form if the impeller remains in a bottom contact position.

In a further example embodiment of the invention, the rotary blood pump may comprise an axial flow pump. The axial flow pump may have one or more magnets implanted in the impeller. When the pump is used as a ventricular assist device, the impeller may be affected by the pulsation of the natural heart. For example, the impeller may be moved back and forth horizontally along the axis of the impeller suspension system. It is desirable to maintain the impeller in a position of dynamic suspension between the supporting structures in order prevent the formation of blood clots or thrombi. A gap between the impeller and the supporting structures of at least 100 microns is necessary to prevent the formation of thrombi. Such an anti-thrombogenic position (dynamic suspension position) may be equated with a normal operating condition of the pump.

Corresponding methods and apparatus are provided for controlling the continuous flow rotary blood pump in accordance with the invention.

BRIEF DESCRIPTION OF THE DRAWINGS

The present invention will hereinafter be described in conjunction with the appended drawing figures, wherein like numerals denote like elements, and.

DETAILED DESCRIPTION OF THE INVENTION

Figure 1:
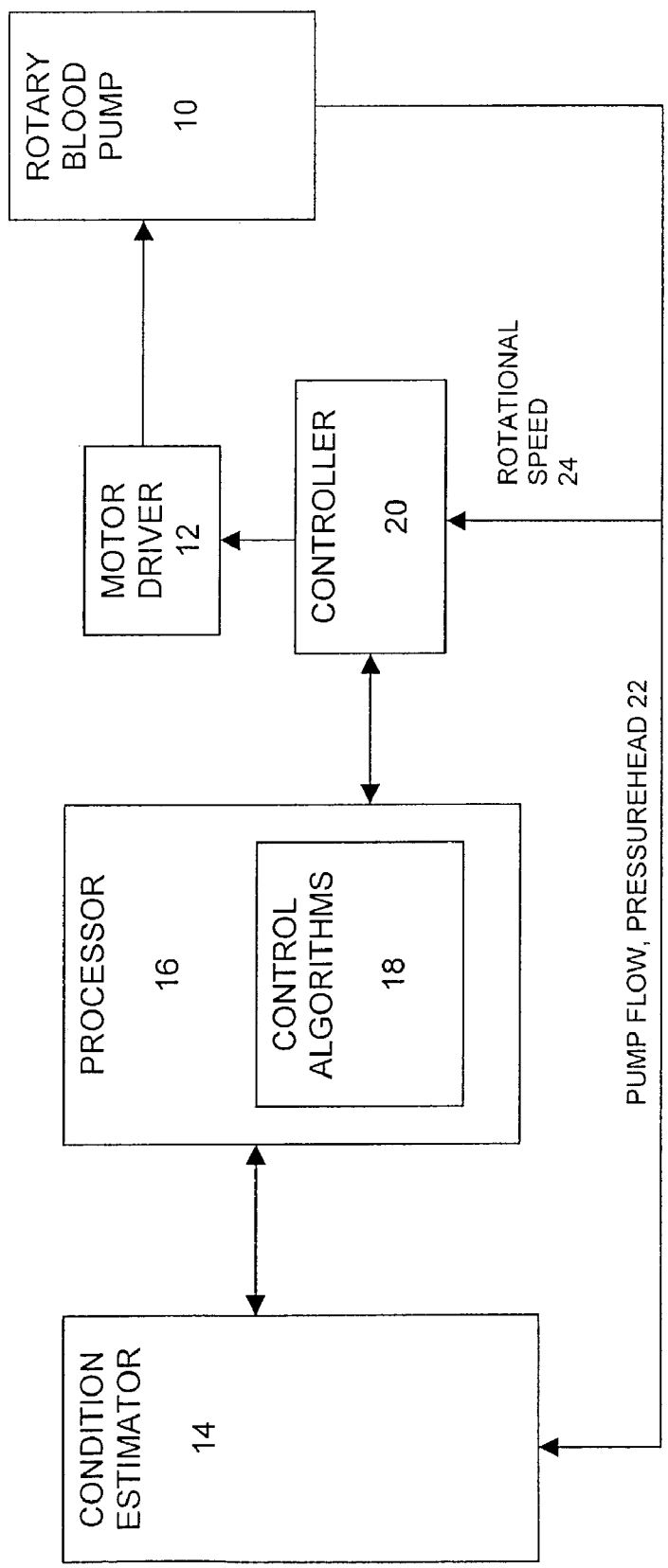
FIG. 1 shows a block diagram of an example embodiment of the invention.

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing a preferred embodiment of the invention. It should be understood that various changes may be made in the function and arrangement of elements without departing from the spirit and scope of the invention as set forth in the appended claims.

The present invention provides control means for a rotary blood pump. In order to operate the pump as a durable anti-thrombogenic rotary blood pump, the pump impeller must be suspended dynamically by either hydraulic or magnetic means when implanted as a bypass pump for a failing heart. The rotary blood pump may comprise, for example, a centrifugal pump or an axial flow pump.

For a centrifugal blood pump, dynamic suspension of the impeller is established when the impeller RPM is synchronized with the beating natural heart. Within a certain RPM range, the impeller achieves dynamic suspension. Typically, for a centrifugal blood pump, the impeller RPM range should be approximately 2,000±1,000 RPM and produce 4 L/min±2 L/min pump flow. The impeller moves toward the top of the pump during the diastolic phase of the natural heart; whereas, during the systolic phase of the natural heart, the impeller moves toward the bottom of the pump. To maintain the dynamic suspension, a specified gap between the male and female bearings is required. Typically, the gap should measure more than 400μ. If this gap is less than 400μ (typically, down to 80μ), effective suspension of the impeller to prevent blood clot formation does not occur. As a result of the impeller movement between the top and bottom housings, stagnant blood areas inside the pump are reduced or eliminated cyclically (typically at around 100 beat/min). Thus, thrombogenic areas inside the blood pump are also eliminated.

In order to further accelerate the reduction of thrombogenic areas inside a blood pump whose inflow tube is not vertical or whose radius of the male (smaller) and female (larger) bearings are different, the swinging motion of the impeller must be generated and synchronized with the natural heart. Typically, this swinging motion of the impeller would be generated when the impeller is at the top contact mode inside of the blood pump.

Dynamic suspension of the impeller of an axial flow blood pump is also possible under proper conditions. Dynamic suspension of the impeller should be synchronized with the beating natural heart so that the impeller moves back and forth horizontally along an axis of the impeller suspension system. Such impeller movements should prevent blood clot formations at the gap between the impeller and its forward-and-backward supporting structure. The gap required for this type of dynamic suspension should be greater than approximately 100μ. As indicated for a centrifugal pump, to eliminate blood clot formation inside an axial flow blood pump, it is imperative that the impeller movement be synchronized with the beating of the natural heart.

Typically, an axial flow blood pump would be operated within the range of 10,000±4,000 RPM in order to generate clinically needed blood flow of 4 L/min±2 L/min. The dynamic suspension of the impeller should be established within this RPM range such that a gap of at least 100μ between the impeller and the supporting structures is maintained during the back and forth movement of the impeller caused by the beating heart. A gap of greater than 100μ is preferred, but may vary depending on pump structure. For example, decoupling may occur due to too large of a gap for the axial flow pump structure.

Suspension of the impeller may also be achieved magnetically. Regardless of the means of suspension, the back and forth movement of the impeller along an axis of the flow pump structure is required to achieve endurance and thrombus-free operation.

In an example embodiment as shown in FIG. 1, a rotary blood pump 10 is provided which has an established normal operating range. The normal operating range may comprise a normal pump flow range and a normal pressure head range. A motor driver 12 is provided to enable driving of the pump 10 at a target rotational speed in accordance with the normal operating range. A condition estimator 14 is provided to enable determination of a current operating condition of the blood pump 10. The current operating condition may comprise a current pump flow, a current pressure head, and a current rotational speed of the pump. A processor 16 is provided to: (1) enable a comparison between the current operating condition and the normal operating range; and (2) enable the selection of an appropriate control algorithm from a plurality of available control algorithms 18 based on the comparison. A controller 20 enables adjustment of the target rotational speed of the pump using the selected control algorithm in order to maintain or recover the normal operating range.

The rotary blood pump 10 may be used as a left ventricular assist device or a right ventricular assist device. The rotary blood pump 10 may be an implantable device or an external device.

Measurements of the current pump flow and the current pressure head (shown collectively as 22) may be provided to the condition estimator 14 to determine the current operating condition. A measurement of the current rotational speed 24 may be provided to the controller 20 as feedback for use in maintaining the target rotational speed of the pump 10. The current pump flow, the current pressure head, and the current rotational speed may be measured by one or more sensors. The one or more sensors may be implantable sensors. Those skilled in the art will appreciate that external sensors may also be used to implement the invention.

The normal operating range may be established by determining a target operating point for the target rotational speed of the pump 10, which provides a target pump flow and a target pressure head. The normal pump flow range may be set as a 20% deviation from the target pump flow. The normal pressure head range may be set as a 25% deviation from the target pressure head.

Figure 2:
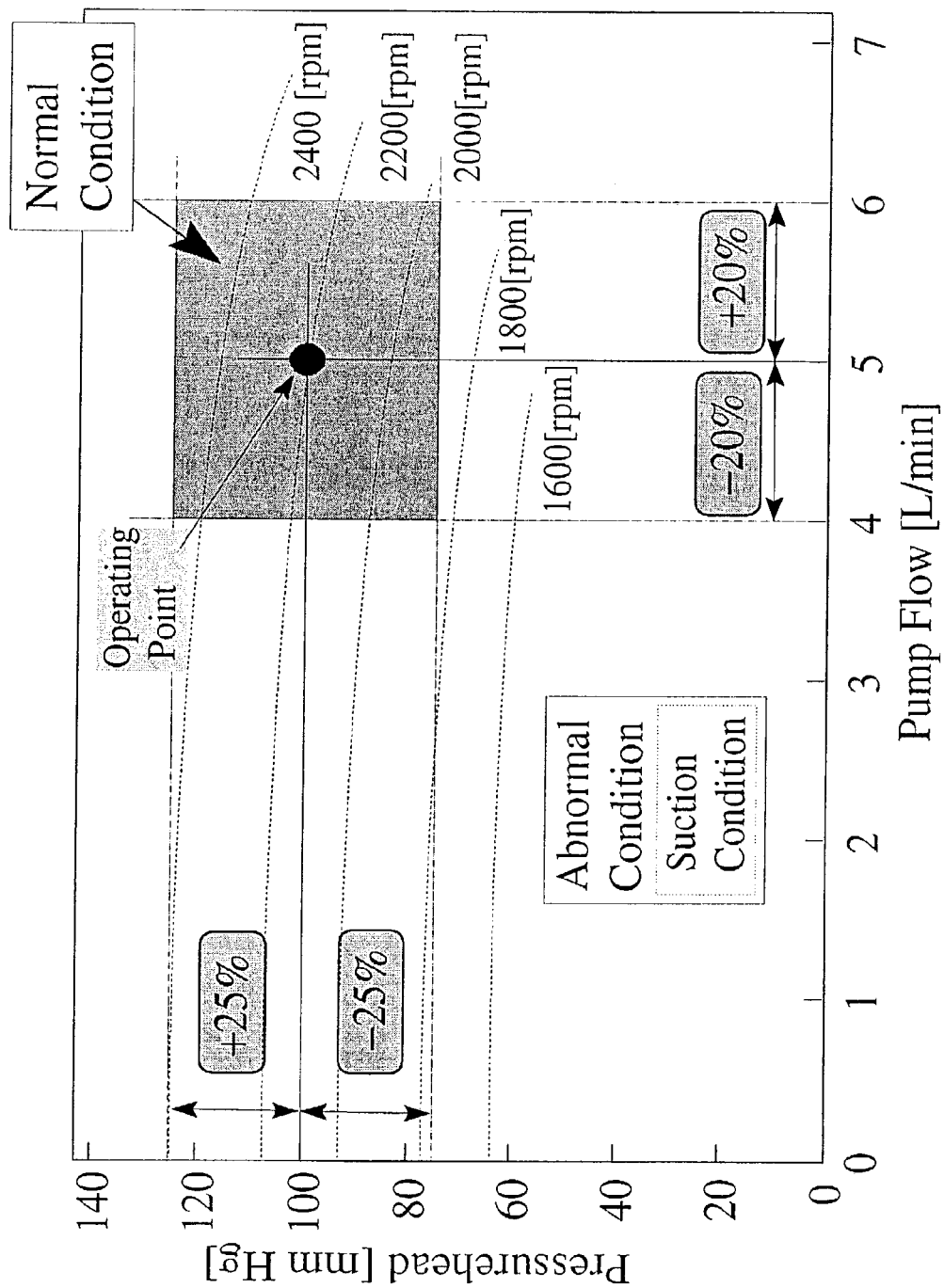
FIG. 2 is a graphical illustration of operating conditions of an example implementation of the invention.

FIG. 2 shows is a plot of pump flow versus pressurehead which illustrates an example of a normal operating range centered about a target operating point. The target operating point in the example shown in FIG. 2 is 100 mm Hg at 5 liters per minute. The normal pump flow range is within a 20% deviation from the target operating point pump flow or within the range of 4 to 6 liters per minute. The normal pressurehead is within a 25% deviation from the target operating point pressurehead or within the range of 75 to 125 mm Hg. Outside of the normal operating range an abnormal condition or a suction condition will be detected.

The normal pump flow range and the normal pressure head range are established by taking into consideration the influences of the body's circadian rhythm, physiological changes of the body, and measured noise. Within the normal operating range, it is assumed that the human body's natural physiological control mechanisms will adjust the current condition by changing the afterload on the pump 10, such as the total peripheral resistance. In this way, the inventive control mechanism does not interfere or compete with the body's autonomic system, unless an abnormal condition is detected. An abnormal condition is one in which the current pump flow or pressurehead are outside of the normal operating range. Under such conditions, unusual problems may result which are beyond the control of the body's physiological control mechanisms.

During the normal operating range, the processor 16 selects a normal operating condition control algorithm. The controller 20 maintains the target rotational speed of the pump 10 by applying proportional and derivative gain control to the pump 10, in accordance with the normal operating condition control algorithm. The proportional and derivative gain control may be applied in accordance with the formula:

$$u = K_p(Y_{target} - Y) + K_d((d/dt)Y_{target} - (d/dt)Y)$$

where u is a driving signal of the pump 10; Y is the rotational speed of the pump 10; $Y_{target}$ is the target rotational speed of the pump 10; $K_p$ is the proportional gain; and $K_d$ is the derivative gain. As an example, $K_p$ may be set to approximately 0.02 and $K_d$ may be set to approximately 0.05.

In the event that the current operating condition is above the normal operating range, the processor 16 selects a first abnormal operating condition control algorithm. The controller decreases the target rotational speed until the normal operating range is recovered, in accordance with the first abnormal operating condition control algorithm. For example, the target rotational speed may be decremented by x rpm every t seconds by the controller until the normal operating range is recovered. In an example embodiment where the pump is a centrifugal pump, x may be set to approximately 150 rpm and t may be set to approximately 5 seconds. In an example embodiment where the pump is an axial flow pump, x may be set to approximately 600 rpm and t may be set to approximately 5 seconds.

In the event that the current operating condition is below the normal operating range, the processor 16 selects a second abnormal operating condition control algorithm. The controller 20 increases the target rotational speed until the normal operating range is recovered, in accordance with the second abnormal operating condition control algorithm. For example, the target rotational speed may be incremented by x rpm every t seconds until the normal operating range is recovered. In an example embodiment where the pump is a centrifugal pump, x may be set to approximately 150 rpm and t may be set to approximately 5 seconds. In an example embodiment where the pump is an axial flow pump, x may be set to approximately 600 rpm and t may be set to approximately 5 seconds.

A suction condition may exist in the event that the normal operating range is not recovered by increasing the target rotational speed. The suction condition may be caused when attempting to recover from the abnormal condition where the current operating condition is below the normal operating range. As described above, in such an abnormal operating condition, the target rotational speed is increased in an attempt to recover the normal operating range. However, if the abnormal condition remains after increasing the target rotational speed, a suction condition may have occurred as a result of overpumping, which results in the inlet port of the pump pulling on the walls of the heart.

In the event of such a suction condition, the processor 16 selects a suction condition control algorithm. The controller 20 releases the suction condition by continuously decreasing the target rotational speed of the pump 10 to obtain a pump flow free from suction and free from overpumping. Once the suction condition is released, the controller 20 gradually increases the target rotational speed of the pump to recover the normal operating range. As an example, when releasing the suction condition, the target rotational speed may be continuously decremented by $x_1$ rpm every t seconds. Once the suction condition is released, the target rotational speed may be continuously incremented by $x_2$ rpm every t seconds. In an example embodiment where the pump is a centrifugal pump, $x_1$ may be set to approximately 150 rpm, $x_2$ may be set to approximately 50 rpm, and t may be set to approximately 5 seconds. In an example embodiment where the pump is a centrifugal pump, $x_1$ may be set to approximately 600 rpm, $x_2$ may be set to approximately 200 rpm, and t may be set to approximately 5 seconds.

Figure 3:
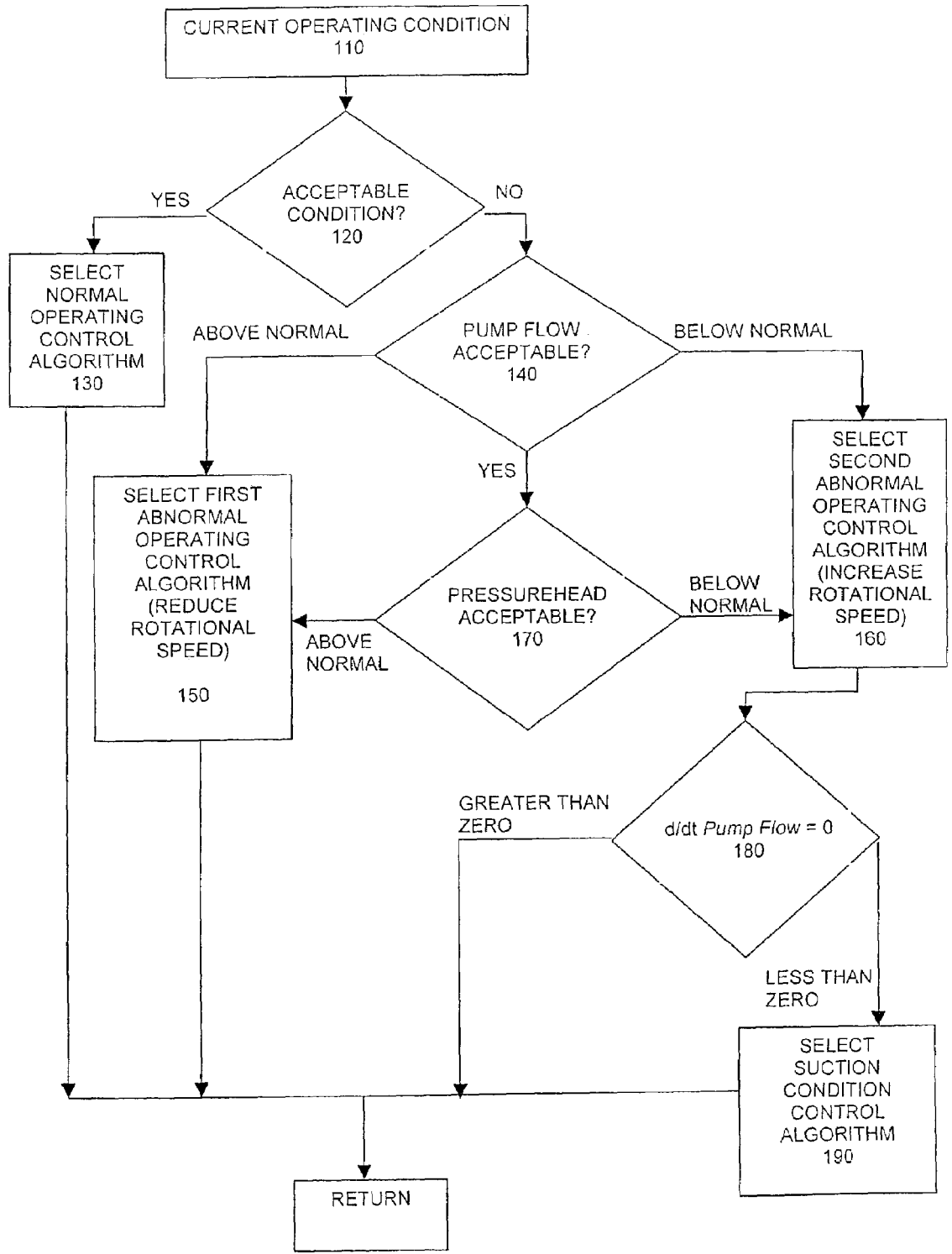
FIG. 3 shows a flowchart of an example embodiment of the invention.

FIG. 3 shows a flowchart of an example embodiment of the invention. The current operating condition 110 is detected, including current pump flow and current pressurehead. The current operating condition is compared with the normal operating range to determine if the current operating condition is acceptable 120. If the current operating condition is acceptable, the normal operating condition control algorithm is selected 130, and the target rotational speed of the pump is maintained as described above in connection with FIG. 1.

If the current operating condition is not acceptable, the current pump flow is compared with the normal pump flow range to determine whether the current pump flow is acceptable 140. If the current pump flow is above the normal pump flow range, the first abnormal operating condition control algorithm is selected 150, and the target rotational speed of the pump is decreased to recover the normal operating range, as described above in connection with FIG. 1. If the current pump flow is below the normal pump flow range, the second abnormal operating condition algorithm is selected 160, and the target rotational speed of the pump is increased to recover the normal operating range, as described above in connection with FIG. 1. If the current pump flow is within the normal pump flow range, the current pressurehead is then compared to the normal pressurehead range to determine if the current pressurehead is acceptable 170. If the current pressurehead is above the normal pressurehead range, the first abnormal operating condition control algorithm is selected 150, and the target rotational speed is reduced. If the current pressurehead is below the normal pressurehead range, the second abnormal condition control algorithm is selected 160, and the target rotational speed is increased.

Once the second abnormal condition control algorithm is selected 160, it is determined whether a suction condition exists by determining the differentiated pump flow 180, if the differentiated pump flow is greater than zero, no suction condition exists. If the differentiated pump flow is less than zero, a suction condition exists and the suction condition control algorithm is selected 190, and the target rotational speed of the pump if first reduced to release the suction condition and then increased to recover the normal operating range as discussed above in connection with FIG. 1.

Figure 4:
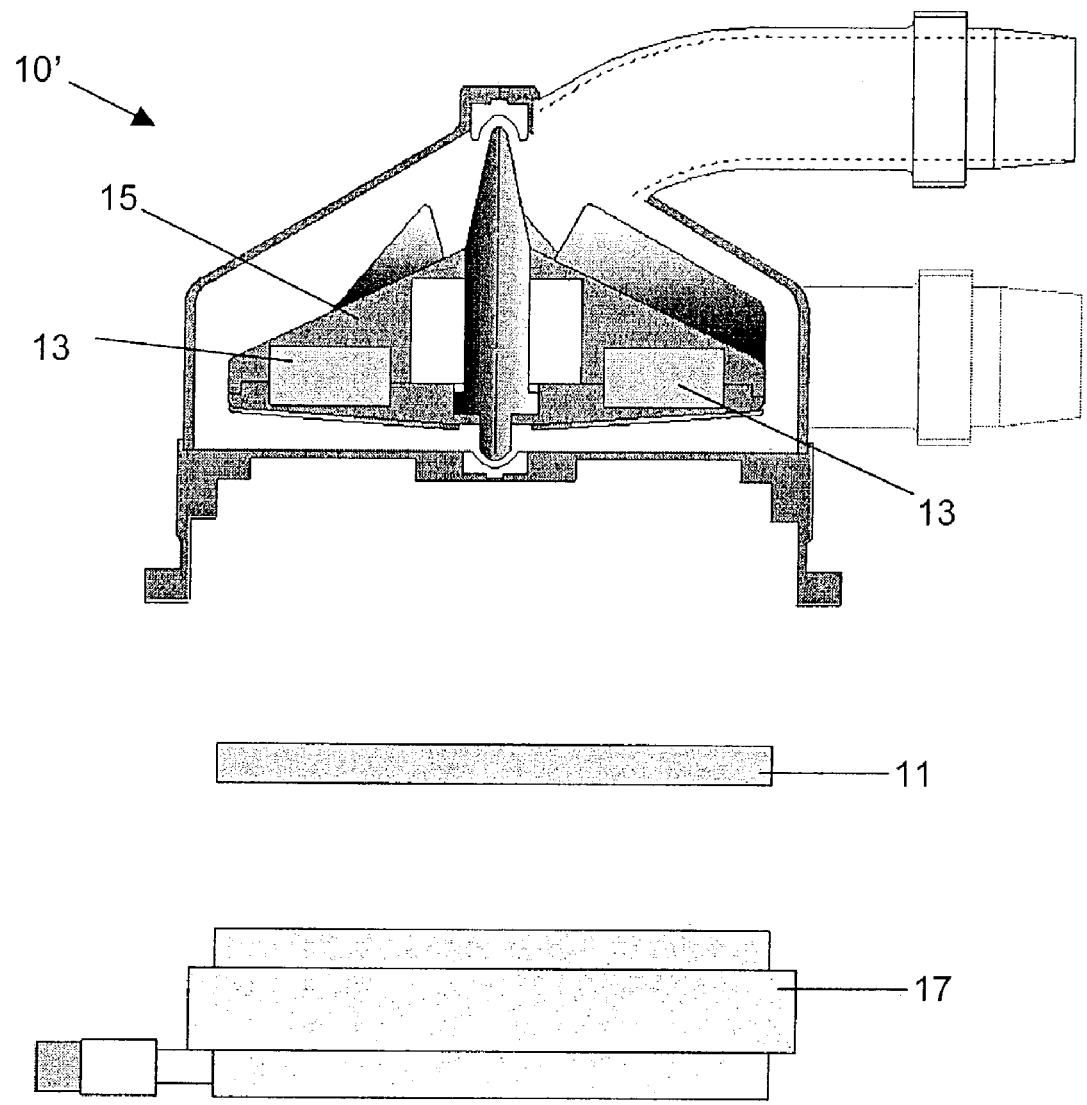
FIG. 4 shows an example embodiment of a centrifugal pump with a Hall sensor in accordance with the invention.

As shown in FIG. 4, the rotary blood pump may be a centrifugal pump 10'. In an example embodiment, the centrifugal pump 10' may have one or more magnets 13 implanted in the impeller 15. When the pump 10' is used as a ventricular assist device, the impeller 15 may be affected by the pulsation of the natural heart. For example, during the diastolic phase of the heart, the impeller 15 may be moved toward a top contact position and in the systolic phase of the heart, the impeller 15 may be moved toward a bottom contact position. The beating of the natural heart may also cause the impeller 15 to move from side to side. It is desirable to maintain the impeller 15 in either a top contact position or in a position of dynamic suspension in order prevent the formation of blood clots or thrombi. Such an anti-thrombogenic position (top contact position or dynamic suspension position) may be equated with a normal operating condition of the pump 10'.

Figure 5:
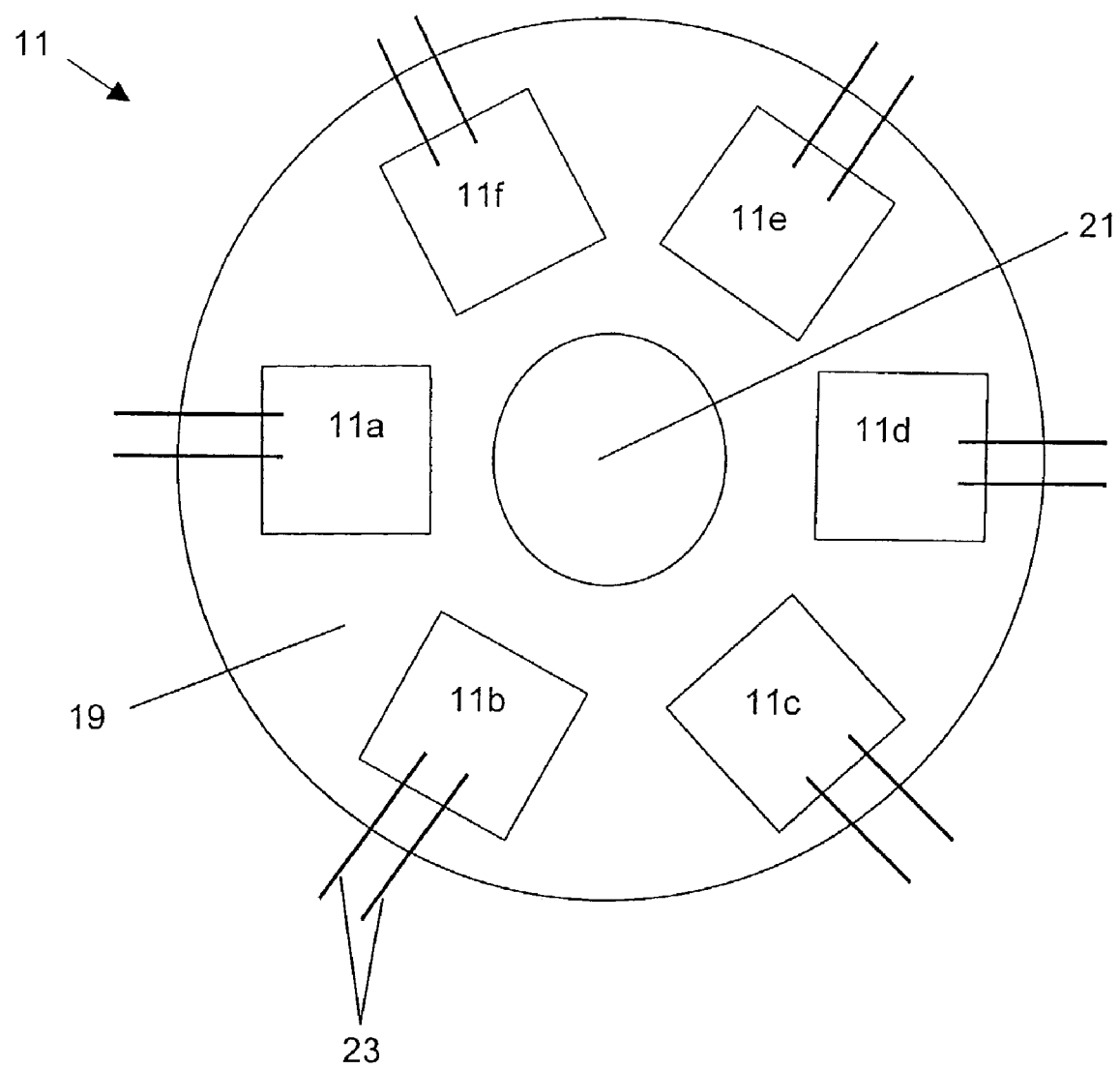
FIG. 5 shows an example Hall sensor configuration for use with the invention.

A Hall sensor 11 may be used to detect the movement in the impeller 15 via the position of the magnets 13 using the well-known Hall effect. The Hall sensor 11 may be positioned between the pump 10' and the pump actuator 17. As shown in FIG. 5, the Hall sensor 11 may comprise multiple Hall sensors 11a-11f arranged in a circular plate 19 with a hole 21 in the center thereof for positioning between the actuator 17 and the pump 10' (as shown in FIG. 4). Each sensor 11a-11f has electrical leads 23 which may be connected, for example, to the controller 20 of FIG. 1.

FIG. 5 shows six Hall sensors 11a-11f. Those skilled in the art will appreciate that any number of Hall sensors may be used to implement the invention, depending on the accuracy of the readings required.

Figure 6:
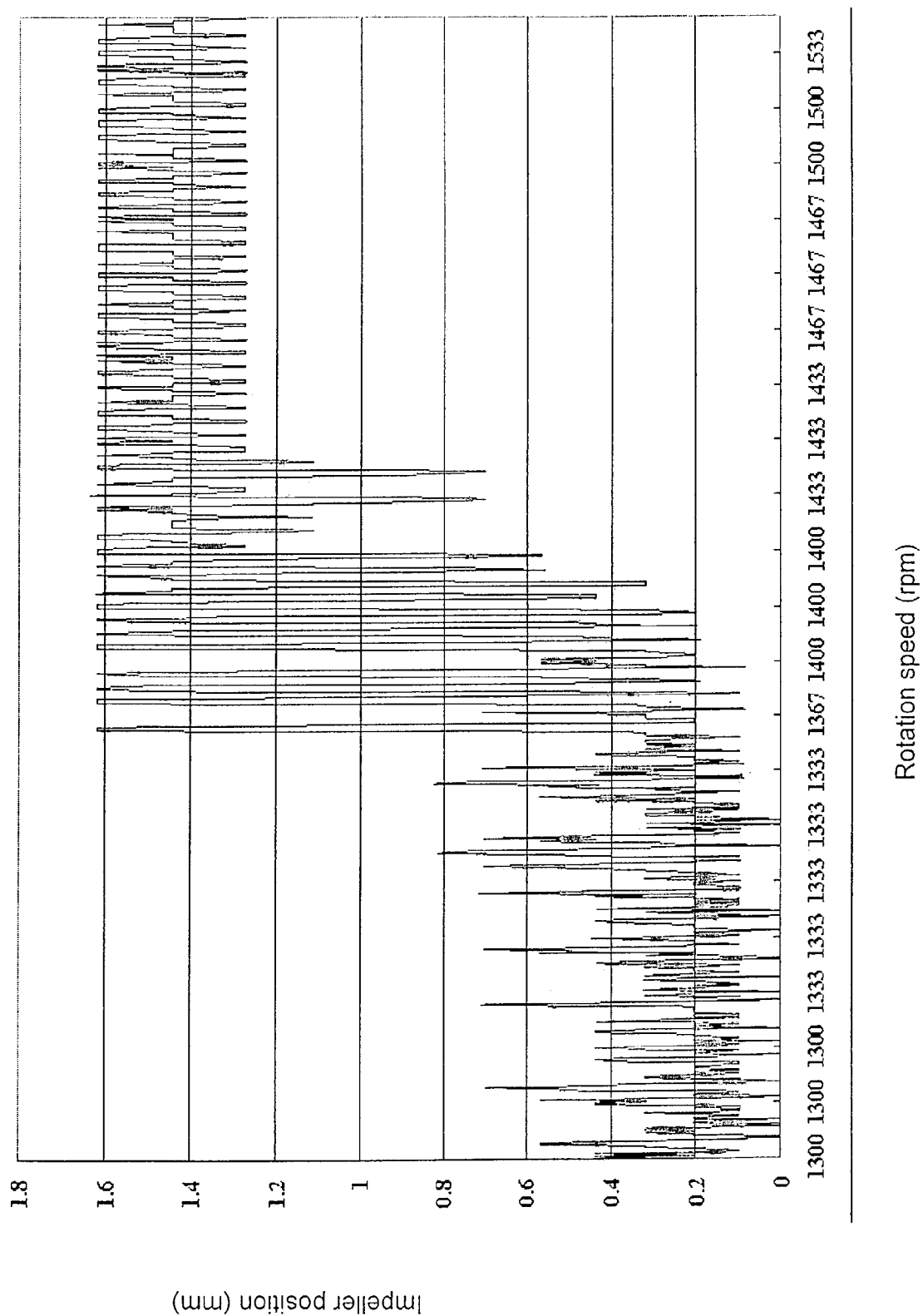
FIG. 6 shows a graph of the impeller position versus rpm of the pump of FIG. 4.

Using the Hall sensor 11, an abnormal pump condition may be detected. For example, when the impeller 15 moves towards the bottom contact position (which position may result in the formation of blood clots) the rpm of the impeller 15 may be adjusted accordingly to compensate for such movement and return the impeller to the anti-thrombogenic position of dynamic suspension or top contact position. As shown in the graph of FIG. 6, increasing the impeller rpm will move the impeller 15 from a bottom contact position toward the top contact position (indicated by the 1.6 mm point in FIG. 6). Thus, a Hall sensor 11 may be used as part of the control mechanism to maintain the impeller 15 in either the top contact position or dynamic suspension in order to prevent the formation of blood clots.

Figure 7:
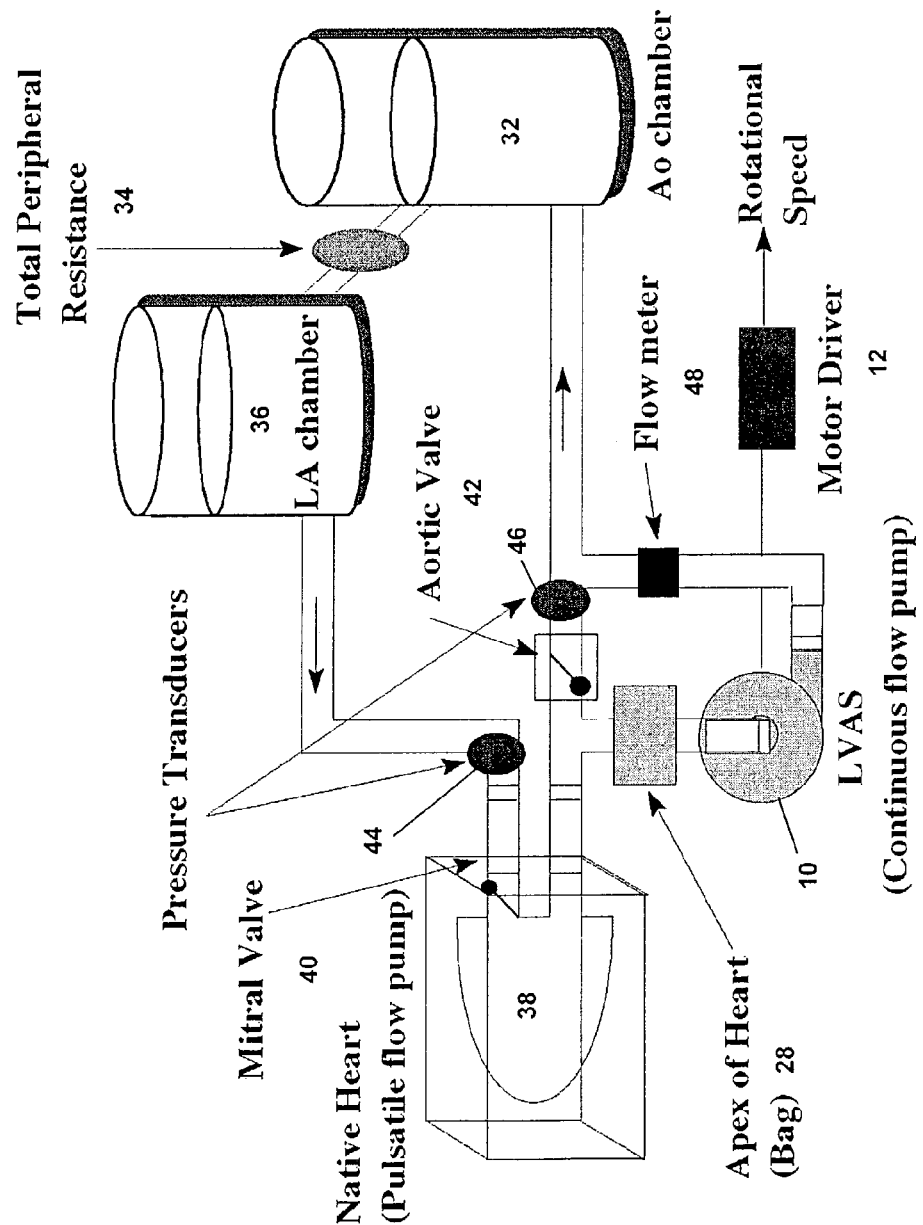
FIG. 7 shows an example model circulation loop used in testing of an embodiment of the invention.

FIG. 7 shows an example of a model left heart circulation loop used in testing of an embodiment of the invention. In the example shown, the continuous flow rotary blood pump 10 is used as a left ventricular assist device and is positioned between the apex of the heart (shown in the model as a bag 28) and the aortic chamber 32. Total peripheral resistance of the heart is provided by a rotating clamping device 34 positioned between the aortic chamber 32 and the left atrial chamber 36. The heart can be modeled as a pulsatile flow pump 38. A mitral valve 40 and an aortic valve 42 are also provided in the model. Pressure transducers 44 and 46 are provided at the distal position of the mitral valve 40 and the distal position of the aortic valve 42, respectively. Pressure transducers 44 and 46 measure pressures between the mitral valve 40 and aortic valve 42. A flow meter 48 measures the flow at the output side of the pump 10. Rotational speed of the pump is controlled by the motor driver 12 as discussed above in connection with FIG. 1.

In testing, the model circulation loop shown in FIG. 7 is filled with water. The bag 28 has a volume of 30 ml and is attached to the inlet port of the pump 10 in order to provide for the simulation of suction in the heart apex. The pressurehead used in testing is the aortic pressure as measured by the pressure transducer 46. Three experiments were performed using a centrifugal pump as a left ventricular assist device in the model of FIG. 7 to test the performance of the inventive system.

Experiment 1

Evaluation of the Controller for Operating Point Control.

In this experiment, the behavior of the convergence of the rotational speed of the pump is evaluated when the target rotational speed is purposely changed up and down. The results of this experiment are shown in FIG. 8.

Figure 8:
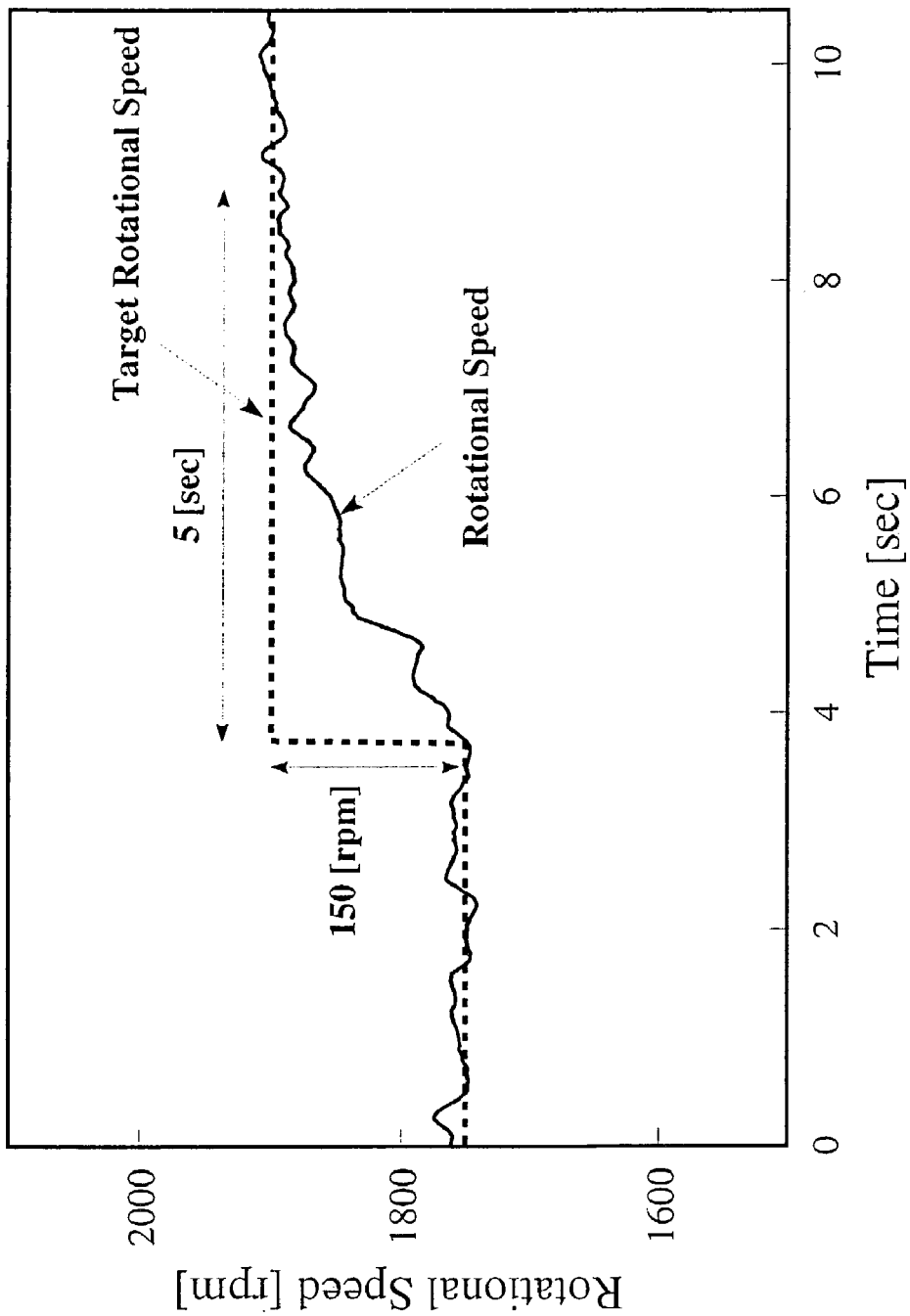
FIG. 8 is a graphical illustration of the convergence response time of an a continuous flow blood pump in accordance with an example embodiment of the invention.

FIG. 8 shows a graph of the rotational speed versus time, which illustrates an example convergence response time of the pump 10 to the proportional and derivative control applied by the normal operating condition algorithm. In the example shown in FIG. 8, the variation of the pump rotational speed is set at 150 rpm per 5 seconds. The target rotational speed of the pump (shown in dashed lines) is shown as being adjusted upwards at the 4 second mark by 150 rpm (i.e. from 1750 rpm to 1900 rpm). In response to the proportional and derivative control, the actual rotational speed of the pump (shown as a solid line) requires approximately 5 seconds to respond and converge on the new target rotational speed of 1900 rpm.

Experiment 2

Evaluation of the Controller for Recovering from Abnormal Condition.

In this experiment, the normal operating condition is changed to an abnormal state by increasing the afterload in the mock circulation loop in order to evaluate the behavior of the controller 20 in recovering from an abnormal condition. The afterload is increased by increasing the total peripheral resistance provided by the clamping device 34.

Figure 9:
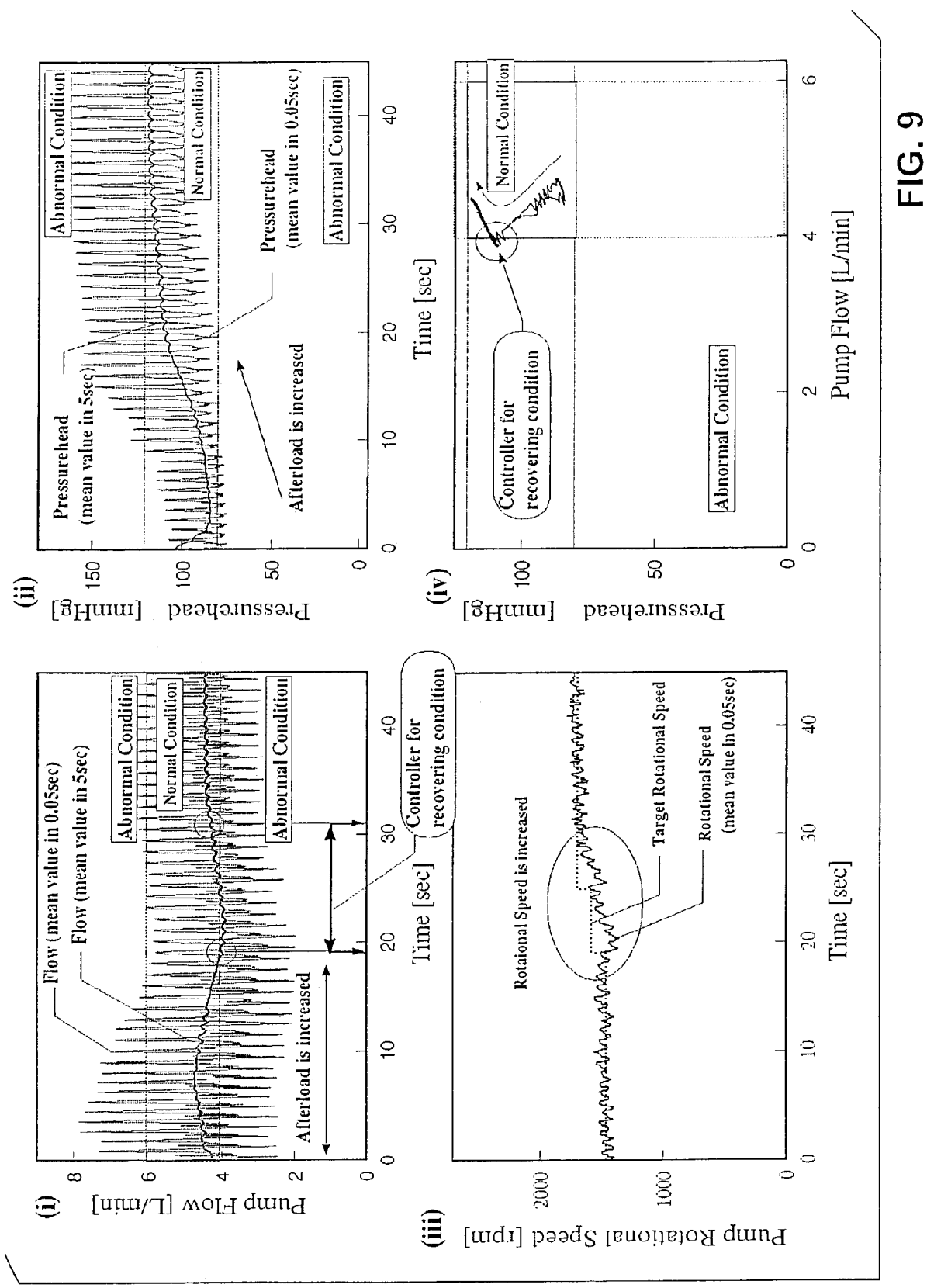
FIG. 9 (FIGS. 9($i$)-9($iv$)) show experimental results for a model implementation of the invention when recovering from an abnormal condition.

FIGS. 9(i) through 9(iv) illustrate the results of this experiment. As shown in FIG. 9(i), by increasing the total peripheral resistance (afterload), the pump flow was decreased. When the pump flow falls under the acceptable range (e.g., 4 L/min as shown in FIG. 9(i)), an abnormal condition is detected and the second abnormal operating condition algorithm is selected by the controller 20. The pressurehead is kept within an acceptable range as shown in FIG. 9(ii). FIG. 9(iii) shows the operation of the second abnormal control algorithm in increasing the target rotational speed of the pump 10 in order to recover normal pump flow. In FIG. 9(ii), the target rotational speed of the pump is increased by 150 rpm every 5 seconds until the normal operating condition is recovered, as shown in FIG. 9(iv).

Experiment 3

Evaluation of Controller for Releasing Pump From a Suction Condition.

To evaluate the controller 20 in recovering from a suction condition, the position of the inlet port of the pump 10 is changed and the afterload is increased. The position of the inlet port was set near the wall of the bag 28.

Figure 10:
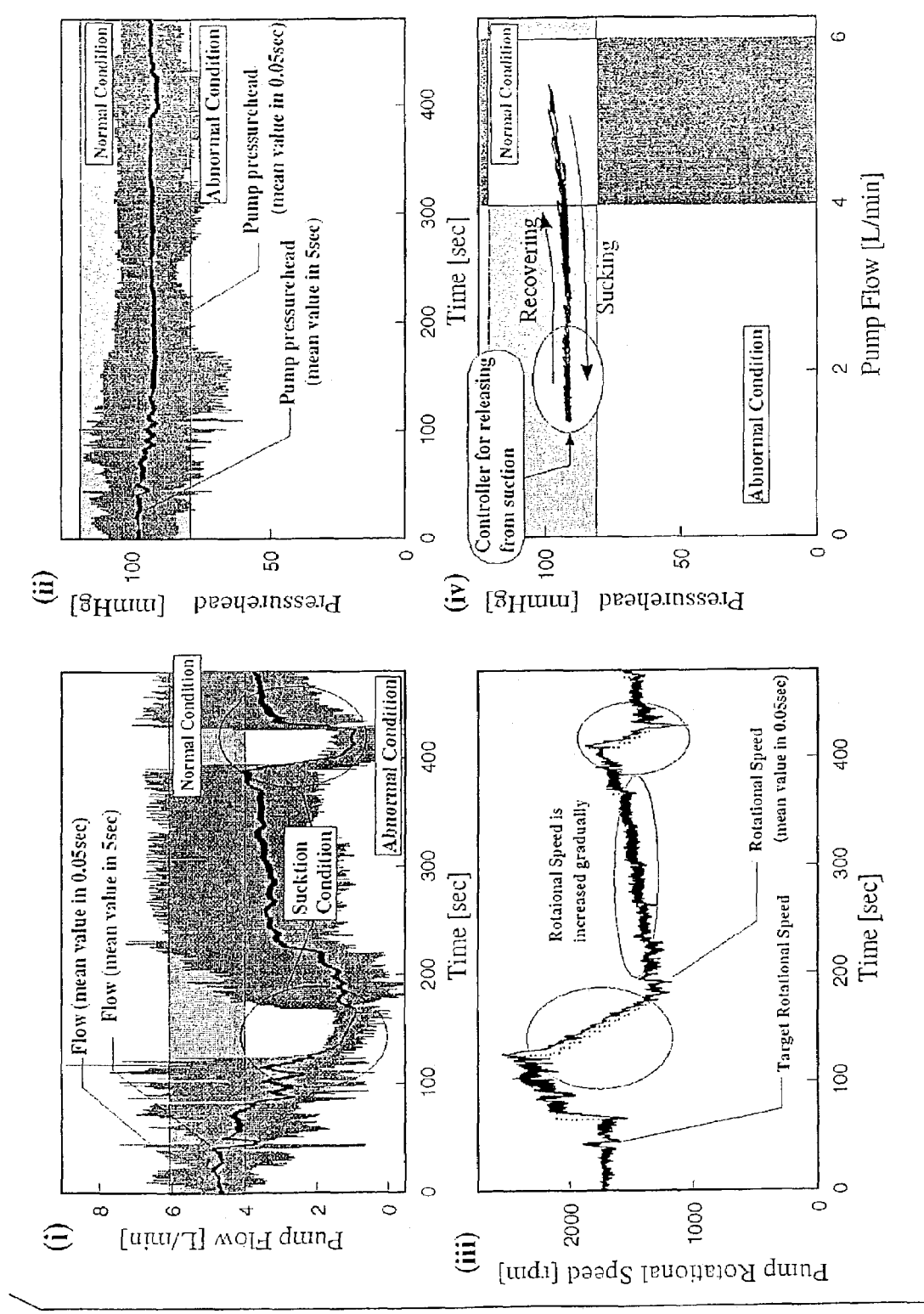
FIG. 10 (FIGS. 10($i$)-10($iv$)) show experimental results for a model implementation of the invention when recovering from a suction condition.

FIGS. 10(i) through 10(iv) illustrate the results of this experiment. As shown in FIG. 10(i), by changing the location of the inlet port and increasing the afterload, a suction condition is generated. Once the current operating condition falls under the normal operating range, the second abnormal operating condition is chosen as discussed above in connection with FIG. 1 and the target rotational speed of the pump is increased. As shown in FIG. 10(ii), the pressurehead can be maintained within the acceptable range even during the occurrence of the suction condition. FIG. 10(iii) shows the increase in the target rotational speed of the pump to recover a normal pump flow range.

However, if the pump flow remains in an abnormal condition, a suction condition will be detected. The suction condition control algorithm will then be selected and the target rotational speed of the pump first decreased to release the suction condition and then increased as shown in FIG. 10(iii). However, since the operational state of the model circulation loop does not change (i.e. the positioning of the inlet port and the afterload which caused the suction condition remain constant absent outside intervention), the normal operating condition of the model loop will not be re-established, as shown in FIG. 10(iv).

As can be seen from FIGS. 10(i) through 10(iv), the controller is able to release the suction condition, but the normal operating condition cannot be re-established. The mock circulation loop will revert to the suction condition, as the state of the mock circulation loop will not change on its own in response to the controller. In an in vivo study, it would be expected that the changes in position of the inlet port will produce a sudden decrease of blood flow at a predetermined rotational speed. The inventive control system will be able to recover from a suction condition, due to the adaptive nature of the body's own physiological control mechanisms.

The experiments described above have shown that, in a model environment, the control system is effective at controlling a rotary blood pump in order to maintain and restore normal operating conditions.

Figure 11:
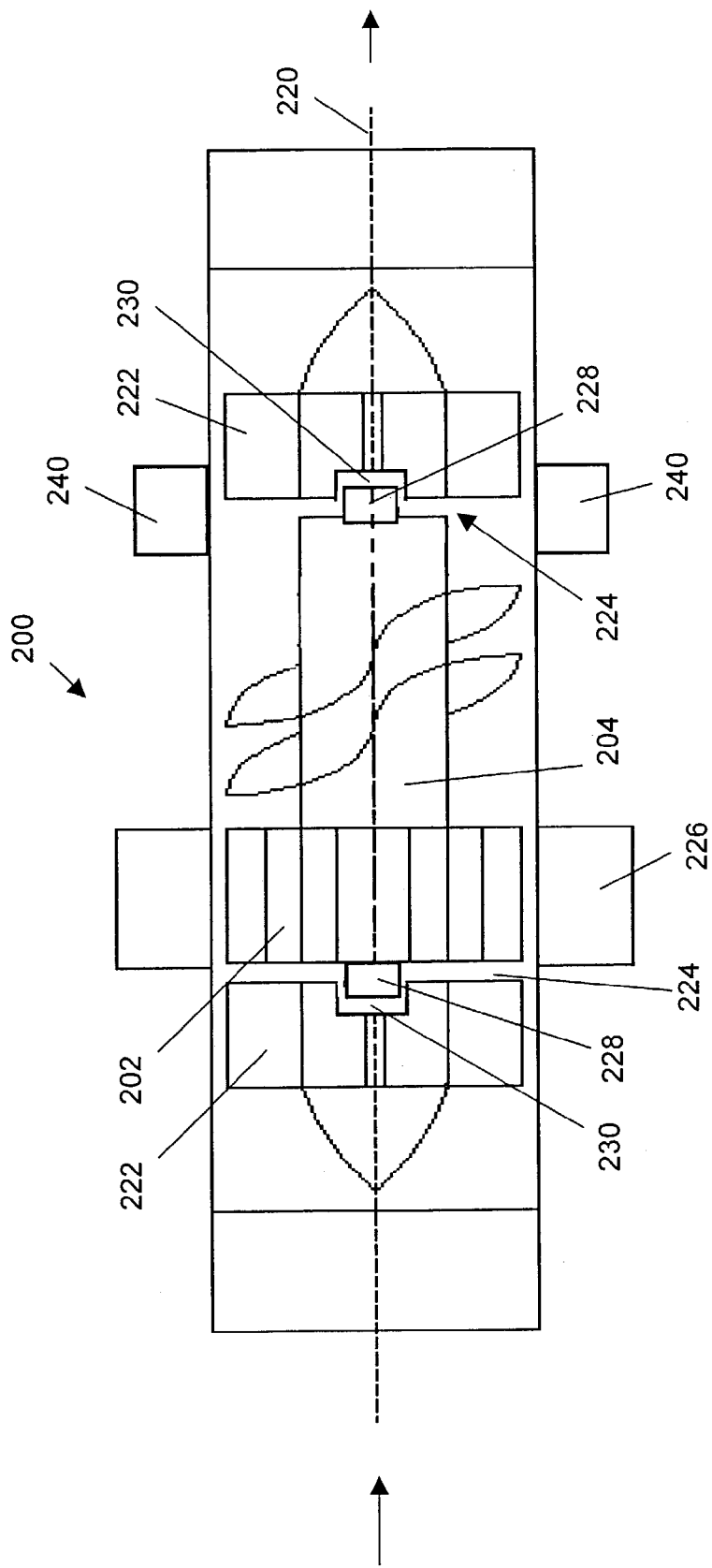
FIG. 11 shows an example embodiment of an axial flow pump in accordance with the invention.

As shown in FIG. 11, the rotary blood pump may comprise an axial flow pump 200. In an example embodiment, the axial flow pump 200 may have one or more magnets 202 implanted in the impeller 204. A motor stator 226 is provided for driving the impeller 202.

When the pump 200 is used as a ventricular assist device, the impeller 204 may be affected by the pulsation of the natural heart. For example, the impeller 204 may be moved back and forth horizontally along the axis 220 of the impeller suspension system. In the case of mechanical suspension of the impeller 204 by bearings 228, a space 230 is required for the bearing movement. It is also desirable to maintain the impeller 204 in a position of dynamic suspension between the supporting structures 222 in order prevent the formation of blood clots or thrombi. A gap 224 between the impeller and the supporting structures 222 of at least 100 microns is necessary to prevent the formation of thrombi. Such an anti-thrombogenic position (dynamic suspension position) may be equated with a normal operating condition of the pump 200.

As with the centrifugal pump described above in connection with FIGS. 4 and 5, a Hall sensor 240 may also be used with the axial flow pump 200 to detect the position of the impeller 204 using the well-known Hall effect.

Dynamic suspension of the impeller 202 may also be achieved magnetically instead of mechanically such that the gap 224 is maintained.

It should now be appreciated that the present invention provides advantageous methods and apparatus for controlling a continuous flow rotary blood pump, such as a centrifugal pump or an axial flow pump.

Although the invention has been described in connection with various illustrated embodiments, numerous modifications and adaptations may be made thereto without departing from the spirit and scope of the invention as set forth in the claims.

What is claimed is:

1. A method for controlling an axial flow rotary blood pump, comprising:
   establishing a normal operating range of the blood pump, said normal operating range comprising a normal pump flow range and a normal pressure head range;
   setting a target rotational speed of said pump in accordance with said normal operating range;
   determining a current operating condition of the blood pump, said current operating condition comprising a current pump flow, a current pressure head, and a current rotational speed of said pump;
   comparing the current operating condition with the normal operating range;
   selecting an appropriate control algorithm from a plurality of available control algorithms based on said comparison; and
   adjusting the target rotational speed of said pump using said selected control algorithm to maintain or recover said normal operating range;
   wherein during said normal operating range:
      a normal operating condition control algorithm is selected; and
      said target rotational speed of said pump is maintained by applying proportional and derivative gain control to said pump.

2. A method in accordance with claim 1, wherein:
   establishing said normal operating range comprises establishing a target operating point for the target rotational speed of the pump which provides a target pump flow and a target pressure head;
   said normal pump flow range is within a 20% deviation from said target pump flow; and
   said normal pressure head range is within a 25% deviation from said target pressure head.

3. A method in accordance with claim 1, wherein:
   said rotary blood pump is used as one of a left ventricular assist device or a right ventricular assist device.

4. A method in accordance with claim 1, wherein:
   measurements of said current pump flow, said current pressure head, and said current rotational speed are used to determine the current operating condition.

5. A method in accordance with claim 4, wherein said current pump flow, said current pressure head, and said current rotational speed are measured by one or more sensors.

6. A method in accordance with claim 5, wherein said one or more sensors are implantable sensors.

7. A method in accordance with claim 1, wherein said proportional and derivative gain control is applied in accordance with the formula:

$$u = K_p(Y_{target} - Y) + K_d((d/dt)Y_{target} - (d/dt)Y);$$

u is a driving signal of said pump;
Y is the rotational speed of the pump;
$Y_{target}$ is the target rotational speed of the pump;
$K_p$ is the proportional gain; and
$K_d$ is the derivative gain.

8. A method in accordance with claim 7, wherein:
$K_p$ is set to approximately 0.02; and
$K_d$ is set to approximately 0.05.

9. A method in accordance with claim 1, wherein said blood pump comprises one of an implantable pump or an external pump.

10. A method in accordance with claim 1, wherein said axial flow pump has magnets implanted in a pump impeller.

11. A method in accordance with claim 10, further comprising:
   detecting a position of said pump impeller using one or more Hall sensors.

12. A method in accordance with claim 11, wherein said one or more Hall sensors detect at least one of vertical or horizontal movement of the pump impeller.

13. A method in accordance with claim 11, further comprising:
   adjusting the rpm of said impeller based on said detecting step in order to maintain the impeller position in a dynamic suspension position.

14. A method in accordance with claim 13, further comprising maintaining a gap between the impeller and supporting structures for the impeller of at least approximately 100 microns.

15. A method in accordance with claim 13, wherein said dynamic suspension is achieved either magnetically or mechanically.

16. A method for controlling an axial flow rotary blood pump, comprising:
   establishing a normal operating range of the blood pump, said normal operating range comprising a normal pump flow range and a normal pressure head range;
   setting a target rotational speed of said pump in accordance with said normal operating range;
   determining a current operating condition of the blood pump, said current operating condition comprising a current pump flow, a current pressure head, and a current rotational speed of said pump;
   comparing the current operating condition with the normal operating range;
   selecting an appropriate control algorithm from a plurality of available control algorithms based on said comparison; and
   adjusting the target rotational speed of said pump using said selected control algorithm to maintain or recover said normal operating range;

wherein in the event that the current operating condition is above said normal operating range:
a first abnormal operating condition control algorithm is selected; and
the target rotational speed is decreased until the normal operating range is recovered.

17. A method in accordance with claim 16, wherein the target rotational speed is decremented by x rpm every t seconds until said normal operating range is recovered.

18. A method in accordance with claim 17, wherein:
x is approximately 600 rpm; and
t is approximately 5 seconds.

19. A method for controlling an axial flow rotary blood pump, comprising:
establishing a normal operating range of the blood pump, said normal operating range comprising a normal pump flow range and a normal pressure head range;
setting a target rotational speed of said pump in accordance with said normal operating range;
determining a current operating condition of the blood pump, said current operating condition comprising a current pump flow, a current pressure head, and a current rotational speed of said pump;
comparing the current operating condition with the normal operating range;
selecting an appropriate control algorithm from a plurality of available control algorithms based on said comparison; and
adjusting the target rotational speed of said pump using said selected control algorithm to maintain or recover said normal operating range;
wherein in the event that the current operating condition is below said normal operating range:
a second abnormal operating condition control algorithm is selected; and
the target rotational speed is increased until the normal operating range is recovered.

20. A method in accordance with claim 19, wherein the target rotational speed is incremented by x rpm every t seconds until said normal operating range is recovered.

21. A method in accordance with claim 20, wherein:
x is approximately 600 rpm; and
t is approximately 5 seconds.

22. A method in accordance with claim 19, wherein a suction condition exists in the event that the normal operating range is not recovered by increasing said target rotational speed, and in the event of such a suction condition;
a suction condition control algorithm is selected;
the suction condition is released by continuously decreasing the target rotational speed of the pump to obtain a pump flow free from suction and free from overpumping; and
once said suction condition is released, the target rotational speed of the pump is gradually increased to recover said normal operating range.

23. A method in accordance with claim 22, wherein:
when releasing the suction condition, the target rotational speed is continuously decremented by $x_1$ rpm every t seconds; and
once the suction condition is released, the target rotational speed is continuously incremented by $x_2$ rpm every t seconds.

24. A method in accordance with claim 23, wherein:
$x_1$ is approximately 600 rpm;
$x_2$ is approximately 200 rpm; and
t is approximately 5 seconds.

25. Apparatus for controlling an axial flow rotary blood pump, comprising:
a rotary blood pump having an established normal operating range, said normal operating range comprising a normal pump flow range and a normal pressure head range;
a motor driver to enable driving of said pump at a target rotational speed in accordance with said normal operating range;
a condition estimator to enable determination of a current operating condition of the blood pump, said current operating condition comprising a current pump flow, a current pressure head, and a current rotational speed of said pump;
a processor to: (1) enable a comparison between the current operating condition and the normal operating range; and (2) enable the selection of an appropriate control algorithm from a plurality of available control algorithms based on said comparison; and
a controller to enable adjustment of the target rotational speed of said pump using said selected control algorithm to maintain or recover said normal operating range;
wherein during said normal operating range:
said processor selects a normal operating condition control algorithm; and
said controller maintains said target rotational speed of said pump by applying proportional and derivative gain control to said pump.

26. Apparatus in accordance with claim 25, wherein:
said normal operating range is established by determining a target operating point for the target rotational speed of the pump which provides a target pump flow and a target pressure head;
said normal pump flow range is within a 20% deviation from said target pump flow; and
said normal pressure head range is within a 25% deviation from said target pressure head.

27. Apparatus in accordance with claim 25, wherein:
said rotary blood pump is used as one of a left ventricular assist device or a right ventricular assist device.

28. Apparatus in accordance with claim 25, wherein:
measurements of said current pump flow and said current pressure head are provided to the condition estimator to determine the current operating condition; and
a measurement of said current rotational speed is provided to said controller.

29. Apparatus in accordance with claim 28, wherein said current pump flow, said current pressure head, and said current rotational speed are measured by one or more sensors.

30. Apparatus in accordance with claim 29, wherein said one or more sensors are implantable sensors.

31. Apparatus in accordance with claim 25, wherein said proportional and derivative gain control is applied in accordance with the formula:

$$u = K_p(Y_{target} - Y) + K_d((d/dt)Y_{target} - (d/dt)Y);$$

u is a driving signal of said pump;
Y is the rotational speed of the pump;
$Y_{target}$ is the target rotational speed of the pump;
$K_p$ is the proportional gain; and
$K_d$ is the derivative gain.

32. Apparatus in accordance with claim 31, wherein:
$K_p$ is set to approximately 0.02; and
$K_d$ is set to approximately 0.05.

33. Apparatus in accordance with claim 25, wherein said blood pump comprises one of an implantable pump or an external pump.

34. Apparatus in accordance with claim 25, wherein said axial flow pump has magnets implanted in a pump impeller.

35. Apparatus in accordance with claim 34, further comprising:
one or more Hall sensors for detecting a position of said pump impeller.

36. Apparatus in accordance with claim 35, wherein said one or more Hall sensors detect at least one of vertical or horizontal movement of the pump impeller.

37. Apparatus in accordance with claim 35, wherein:
the rpm of the impeller is adjusted based on the impeller position as detected by the one or more Hall sensors in order to maintain the impeller position in a dynamic suspension position.

38. Apparatus in accordance with claim 37, wherein a gap is maintained between the impeller and supporting structures for the impeller of at least approximately 100 microns.

39. Apparatus in accordance with claim 37, wherein said dynamic suspension is achieved either magnetically or mechanically.

40. Apparatus for controlling an axial flow rotary blood pump, comprising:
a rotary blood pump having an established normal operating range, said normal operating range comprising a normal pump flow range and a normal pressure head range;
a motor driver to enable driving of said pump at a target rotational speed in accordance with said normal operating range;
a condition estimator to enable determination of a current operating condition of the blood pump, said current operating condition comprising a current pump flow, a current pressure head, and a current rotational speed of said pump;
a processor to: (1) enable a comparison between the current operating condition and the normal operating range; and (2) enable the selection of an appropriate control algorithm from a plurality of available control algorithms based on said comparison; and
a controller to enable adjustment of the target rotational speed of said pump using said selected control algorithm to maintain or recover said normal operating range;
wherein in the event that the current operating condition is above said normal operating range:
said processor selects a first abnormal operating condition control algorithm; and
said controller decreases the target rotational speed until the normal operating range is recovered.

41. Apparatus in accordance with claim 40, wherein the target rotational speed is decremented by x rpm every t seconds until said normal operating range is recovered.

42. Apparatus in accordance with claim 41, wherein:
x is approximately 600 rpm; and
t is approximately 5 seconds.

43. Apparatus for controlling an axial flow rotary blood pump, comprising:
a rotary blood pump having an established normal operating range, said normal operating range comprising a normal pump flow range and a normal pressure head range;
a motor driver to enable driving of said pump at a target rotational speed in accordance with said normal operating range;
a condition estimator to enable determination of a current operating condition of the blood pump, said current operating condition comprising a current pump flow, a current pressure head, and a current rotational speed of said pump;
a processor to: (1) enable a comparison between the current operating condition and the normal operating range; and (2) enable the selection of an appropriate control algorithm from a plurality of available control algorithms based on said comparison; and
a controller to enable adjustment of the target rotational speed of said pump using said selected control algorithm to maintain or recover said normal operating range;
wherein in the event that the current operating condition is below said normal operating range:
said processor selects a second abnormal operating condition control algorithm; and
said controller increases the target rotational speed until the normal operating range is recovered.

44. Apparatus in accordance with claim 43, wherein the target rotational speed is incremented by x rpm every t seconds until said normal operating range is recovered.

45. Apparatus in accordance with claim 44, wherein:
x is approximately 600 rpm; and
t is approximately 5 seconds.

46. Apparatus in accordance with claim 43, wherein a suction condition exists in the event that the normal operating range is not recovered by increasing said target rotational speed, and in the event of such a suction condition;
said processor selects a suction condition control algorithm;
said controller releases the suction condition by continuously decreasing the target rotational speed of the pump to obtain a pump flow free from suction and free from overpumping; and
once said suction condition is released, said controller gradually increases the target rotational speed of the pump to recover said normal operating range.

47. A method in accordance with claim 46, wherein:
when releasing the suction condition, the target rotational speed is continuously decremented by $x_1$ rpm every t seconds; and
once the suction condition is released, the target rotational speed is continuously incremented by $x_2$ rpm every t seconds.

48. Apparatus in accordance with claim 47, wherein:
$x_1$ is approximately 600 rpm;
$x_2$ is approximately 200 rpm; and
t is approximately 5 seconds.

* * * * *